(12) United States Patent
McBride et al.

(10) Patent No.: US 7,407,671 B2
(45) Date of Patent: Aug. 5, 2008

(54) TEMPERATURE CONTROLLED SOLUTE DELIVERY SYSTEM

(75) Inventors: James F. McBride, Cincinnati, OH (US); Stevin H. Gehrke, Manhattan, KS (US); John P. Fisher, Houston, TX (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 859 days.

(21) Appl. No.: 10/787,233

(22) Filed: Feb. 27, 2004

(65) Prior Publication Data

US 2004/0228922 A1  Nov. 18, 2004

Related U.S. Application Data

(62) Division of application No. 09/576,714, filed on May 23, 2000, now Pat. No. 6,733,788, which is a division of application No. 09/050,927, filed on Mar. 31, 1998, now abandoned.

(51) Int. Cl.
  *A61K 9/16* (2006.01)
  *A61K 9/14* (2006.01)
  *A61K 47/00* (2006.01)
  *A61K 25/00* (2006.01)

(52) U.S. Cl. .................. 424/488; 424/486; 424/781; 514/772.1; 514/781

(58) Field of Classification Search ............ None
  See application file for complete search history.

(56) References Cited

U.S. PATENT DOCUMENTS

| | | | |
|---|---|---|---|
| 4,481,323 A | 11/1984 | Sterling | |
| 4,515,593 A | 5/1985 | Norton | |
| 4,589,873 A | 5/1986 | Schwartz et al. | |
| 4,603,152 A | 7/1986 | Laurin et al. | |
| 4,769,013 A | 9/1988 | Lorenz et al. | |
| 4,830,855 A | 5/1989 | Stewart | |
| 4,912,032 A | 3/1990 | Hoffman et al. | |
| 4,950,256 A | 8/1990 | Luther et al. | |
| 5,000,955 A | 3/1991 | Gould et al. | |
| 5,026,607 A | 6/1991 | Kiezulas | |
| 5,041,100 A | 8/1991 | Rowland et al. | |
| 5,091,205 A | 2/1992 | Fan | |
| 5,102,402 A | 4/1992 | Dror et al. | |
| 5,135,516 A | 8/1992 | Sahatjian et al. | |
| 5,152,758 A | 10/1992 | Kaetsu et al. | |
| 5,171,217 A | 12/1992 | March et al. | |
| 5,221,698 A | 6/1993 | Amidon et al. | |
| 5,304,121 A | 4/1994 | Sahatjian | |
| 5,417,983 A | 5/1995 | Nagase et al. | |
| 5,516,808 A | 5/1996 | Sawaya | |
| 5,525,348 A | 6/1996 | Whitbourne et al. | |
| 5,580,573 A | 12/1996 | Kydnieus et al. | |
| 5,603,955 A | 2/1997 | Gehrke et al. | |
| 5,607,417 A | 3/1997 | Batich et al. | |
| 5,652,225 A | 7/1997 | Isner | |
| 5,674,192 A | 10/1997 | Sahatjian et al. | |
| 5,674,521 A | 10/1997 | Gehrke et al. | |
| 5,840,338 A | 11/1998 | Roos | |
| 5,932,248 A | 8/1999 | Chen et al. | |
| 6,733,788 B2 * | 5/2004 | McBride et al. ............ 424/488 |

FOREIGN PATENT DOCUMENTS

| | | |
|---|---|---|
| EP | 0 177 983 | 4/1986 |
| EP | 0 379 156 A2 | 7/1990 |
| GB | 2 112 646 | 7/1983 |
| WO | WO 91/08790 | 6/1991 |
| WO | WO 98/02114 | 1/1998 |
| WO | WO 98/46287 | 10/1998 |

OTHER PUBLICATIONS

McBride et al., M. S. Thesis, 1996.

Y. Osada et al., Intelligent Gels, Scientific American, May 1993.

Anna Gutowska et al., Journal of Biomedical Materials Research, 1995, "Heparin release from thermosensitive polymer coatings: In vivo studies", vol. 29, pp. 811-821.

Hsieh, D., "Controlled Release Systems: Fabrication Technology,"vol. II, 1988.

Gehrke, S., Lyu, L-H, Barnthouse, C., "Dewatering Fine Coal Slurries by Gel Extraction," Separation Science and Technology, 33(10), pp. 1467-1485, 1998.

Kabra, B, Gehrke, S H., and Spontak, R.J., "Microporous, Responsive Hydroxypropyl Cellulose Gles. 1. Synthesis and Microstructure," Macromolecules, vol. 31, No. 7, pp. 2166-2173 (1998).

(Continued)

*Primary Examiner*—Raymond J Henley, III
(74) *Attorney, Agent, or Firm*—Kenyon & Kenyon LLP

(57) ABSTRACT

A system for delivering solute to a target location within a mammalian body, the system including a medical device, a thermosensitive cellulose gel structure over the medical device, and a biologically active solute within said gel structure. The gel structure deswells and expels the biologically active solute with an increase in gel temperature. The invention includes a method of delivering solute to a target location, where the method includes the steps of providing a thermosensitive cellulose gel structure, wherein the gel structure is loaded with a solute; positioning the loaded gel structure to the target location; and increasing the temperature of the loaded gel structure.

12 Claims, 11 Drawing Sheets

OTHER PUBLICATIONS

Bae et al., "Thermo-sensitive polymers as on-off switches for drug release," Makromol. Chem. Rapid Commun . . . , 1987, 8:481-485.

Bae, "Stimuli-Sensitive Drug Delivery, "*Controlled Drug Delivery: Challenges and Strategies*, 147-162, American Chemical Society, Washington D.C., 1997.

Gehrke et al., "Factors Determining Hydrogel Permeability,"*Bioartifical Organs: Science, Medicine and Technology*, Annals of the New York Academy of Sciences, 1997. 831:179-206.

McBride, "Solute Permeability and Release from Thermosensitive Gels," Master of Science Thesis, University of Cincinnati, Division of Research and Advanced Studies, 1996.

Yoshida et al., "Drug Release Profiles in the Shrinking Process of Thermoresponsive Poly(N-isopropylacrylamide-co-alkyl methacrylate) Gels," Ind. Eng. Chem. Res., 1992, 31:2339-2345.

Gutowska, et al., "Thermosensitive Interpenetrating Polymer Networks: Synthesis, Characterization, and Macromolecular Release," Macromolecules, 1994, 27:4167-4175.

Dinarvand et al., "The use of thermoresponsive hydrogels for on-off release of molecules." Journal of Controlled Release, 1995, 36:221-227.

Harsh et al., "Controlling the swelling characteristics of temperature-sensitive cellulose ether hydrogels," Journal of Controlled Release, 1991, 17:175-186.

Gehrke et al., "Effect of Synthesis Conditions on Properties of Poly(N-isopropylacrylamide) Gels," Polymer International, 1992, 29:29-36.

Fram et al., "Localized Intramural Drug Delivery During Balloon Angioplasty Using Hydrogel-Coated Balloons and Pressure-Augmented Diffusion," J. Am. Coll. Cardiol., 1994, 23: 1570-1577.

Gutowska et al., "Heparin release from thermosensitive polymer coatings: in vivo studies," J. Biol. Materials Research, 1995, 29:811-821.

Fram et al., "Localized Intramural Delivery of a Marker Agent During Balloon Angioplasty: A New Technique Using Hydrogel-Coated Balloons and Active Diffusion," Abstracts From the 65th Scientific Session, Oct. 1992, Supplement I, 86/4:1-380, Abstract 1515.

Nunes et al., "Hydrogel-Coated PTC Balloon Catheter Delivery of an Antithrombin Inhibits Platelet-Dependent Thromosisi," Abstracts From the 65th Scientific Session, Oct. 1992, Supplement I, 86/4:1-380, Abstract 1516.

Fisher, "The Permeability of Temperature Responsive Cellulose Ether Hydrogels," Master of Science Thesis, University of Cincinnati, Division of Research and Advanced Studies, 1997.

* cited by examiner

TEMPERATURE CONTROLLED SOLUTE DELIVERY SYSTEM

RELATED APPLICATIONS

This application is a divisional of U.S. application Ser. No. 09/576,714, filed on May 23, 2000, which is now U.S. Pat. No. 6,733,788, which is a divisional of U.S. application Ser. No. 09/050,927, filed Mar. 31, 1998, which is now abandoned, which are incorporated herein in their entirety by reference thereto.

FIELD OF THE INVENTION

The present invention relates to thermosensitive hydrogels loaded with solute materials, and more particularly, to the delivery of biologically active solute materials to target locations within a mammalian body using thermosensitive cellulose gels.

BACKGROUND OF THE INVENTION

Hydrogels are crosslinked networks of biological, synthetic, or semi-synthetic polymers. Because hydrogel polymer chains are held together by crosslinks, hydrogels behave like solids rather than liquids, despite the fact that they contain at least 20% water by weight. A significant property of hydrogels is the equilibrium degree of swelling ("Q"), which is the amount of water absorbed by the gel expressed as the ratio of swollen gel volume (or mass) to dry gel volume (or mass). Many hydrogels are responsive to external stimuli in that they expel or absorb water in response to changes in pH, electric field, light intensity, pressure, indirect chemical stimuli, and temperature. The resulting change in hydrogel water content results in a corresponding reversible change in volume.

Hydrogels have many technological uses in both medical and non-medical fields. Owing to their often good biocompatibility and easily adjustable permeability, hydrogels have been used in a range of biomedical applications including contact lenses, diapers, soft and hard tissue prostheses and bioartificial organs.

One of the most interesting potential biomedical applications for hydrogels is the use of these gels as vehicles for the delivery of biologically active solutes. In such an application, the biologically active solute is absorbed into the gel as a solute and thereafter released from the gel over time. The localized delivery of biologically active materials is described, for example, in U.S. Pat. Nos. 5,304,121, 5,674, 192 and 5,588,962, and in A. Gutowska et al., "Heparin Release from Thermosensitive Polymer Coatings: In vivo Studies," 29 *J. Biomed. Matls. Res.* 811 (1995), each of which is incorporated herein by reference.

Hydrogels are attractive for the delivery of peptide or protein-drugs because they provide a hydrophilic environment for proteins and thus help preserve their activities. Most therapeutic proteins are vulnerable to the proteases in the digestive tract and also have difficulty crossing the skin and other barrier membranes. Implantable drug release systems are thus a viable alternative for delivering therapeutic proteins. Recently, pH-sensitive hydrogels based on poly (N-isopropylacrylamide) ("PNIPA") have been proposed for enteric drug delivery. In such a system, the gel is collapsed at gastric pH for the negligible release of protein, whereas the gel swells at enteric pH thus permitting sustained release within the intestines.

Hydrogels that undergo reversible volume changes in response to changes in temperature are known as thermosensitive gels. These gels shrink at a transition temperature that is related to the lower critical solution temperature ("LCST") of the linear polymer from which the gel is made. Specifically, typical thermosensitive gels have an affinity for water and thus swell at temperatures below the transition temperature, whereas they expel water and thus shrink or "deswell" at temperatures above the transition temperature. Thermosensitive hydrogels are potentially of significant utility in biomedical applications, particularly as a means for localized drug delivery. PNIPA is an example of a known thermosensitive hydrogel, as described in R. Dinarvand et al., "The Use of Thermosensitive Hydrogels for On-off Release of Molecules," 36 *J. Controlled Release* 221 (1995); A. Gutowska et al., "Thermosensitive Interpenetrating Polymer Networks: Synthesis, Characterization, and Macromolecular Release," 27 *Macromolecules* 4167 (1994); R. Yoshida et al., "Drug Release Profiles in the Shrinking Process of Thermoresponsive Poly(N-isopropylacrtlamide-co-alkyl methacrylate) Gels," 31 *Ind. Eng. Chem. Res.* 2339 (1992); and Y. Han Bae et al., "Thermo-sensitive Polymers as On-off Switches for Drug Delivery," 8 *Makromol. Chem., Rapid Commun.* 481 (1987), each of which is incorporated herein by reference.

Known thermosensitive hydrogels such as PNIPA generally become impermeable to solute when these gels deswell. Consequently, such hydrogels are not applicable to drug delivery systems wherein drug release corresponds to an increase in temperature to above the hydrogel transition temperature. In addition, known thermosensitive hydrogels (e.g., PNIPA) are generally of questionable or uncertain biocompatibility to be safely used in desired drug delivery applications, and as such, FDA approval for the use of PNIPA as part of solute delivery systems remains questionable. Moreover, means for the use of thermosensitive hydrogels in specific localized drug delivery systems have not been detailed in the literature.

SUMMARY OF THE INVENTION

In one aspect, the present invention includes a system for delivering solute to a target location within a mammalian body, the system comprising a medical device, a thermosensitive cellulose gel structure over the medical device, and a solute within the gel structure. In one embodiment, the gel deswells and expels the solute with an increase in gel temperature.

In another aspect, the present invention includes a method of delivering solute to a target location, the method comprising the steps of providing a thermosensitive cellulose gel structure, wherein the gel structure is loaded with a solute, positioning the loaded gel structure to the target location, and increasing the temperature of the loaded gel structure from an initial temperature to a temperature higher than the initial temperature. In one embodiment, the step of increasing the temperature of the loaded gel structure results in the deswelling of the gel, thus releasing the solute. In a further embodiment, the target location is located within a mammalian body, the substrate is a medical device, the solute is a biologically active solute, and the step of increasing the temperature of the loaded gel structure is accomplished by exposing the loaded gel structure to body temperature or an external fluid.

DETAILED DESCRIPTION

Figure 1A:
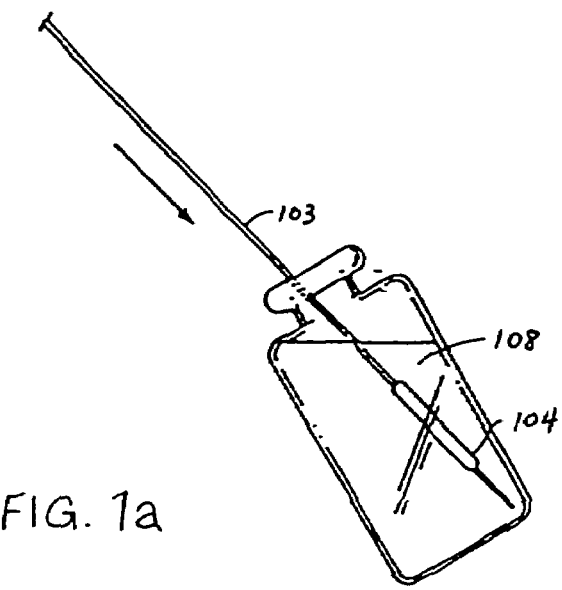
FIG. 1*a* shows an embodiment of the present invention in which a biologically active solute is impregnated into a hydrogel-coated balloon catheter.

The present invention includes a temperature controlled solute delivery system comprising at least one thermosensitive cellulose gel structure. The present invention is described with specific reference to cellulose ether gels, which are the preferred cellulose gels of the present invention. The inventors have found that it is possible to use such gels in solute delivery systems wherein a solute is impregnated into a gel while in its low temperature, expanded state, and is then released from the gel when the gel is placed into its high temperature, deswelled state. Although typical thermosensitive gels are generally known to shrink when they are heated, the inventors have found that they do not exhibit similar solute release properties. For example, solute-loaded PNIPA gels substantially trap solute within the gel when they shrink, whereas the inventors have surprisingly found that solute-loaded thermosensitive cellulose gels release solute when they shrink. This is due to the fact that previously reported thermosensitive gels become impermeable to solute as they shrink, whereas the gels of the present invention remain permeable even when they shrink. Therefore, in contrast to previously reported thermosensitive gels, the gels of the present invention release solute upon shrinking in a sustained, convective release pulse such that substantially all of the loaded solute is released in a relatively short period of time. Moreover, the release of solute from shrinking gels is generally significantly faster than for non-shrinking gels.

As used herein, "cellulose ether gel" includes any crosslinked thermosensitive hydrogel formed by the partial or complete etherification of the hydroxyl groups in a cellulose molecule. Such gels include, for example, hydroxypropyl cellulose ("HPC") gels, hydroxypropylmethyl cellulose ("HPMC") gels, ethylhydroxyethyl cellulose ("EHEC") gels, carboxymethyl cellulose ("CMC") gels, hydroxyethyl cellulose ("HEC") gels., methyl cellulose ("MC") gels, ethyl cellulose ("EC") gels, propyl cellulose ("PC") gels, butyl cellulose ("BC") gels, and the like and blends thereof. These gels are physically or chemically crosslinked. Preferred crosslinkers for these gels include, for example, divinylsulfone ("DVS") and polyethylene glycol vinylene sulfone ("PEG-VS$_2$").

The temperature control solute delivery systems of the present invention are of particular benefit to medical device applications such as, for example, balloon angioplasty units. While the present invention may be described with specific reference to use with a balloon catheter, the present invention is suitable for use with any medical device where the localized delivery of biologically active solute is desired.

Currently, the two principle forms of intervention for coronary artery disease are coronary artery bypass surgery and balloon angioplasty. Balloon angioplasty uses fluid pressure to expand a flexible balloon which is catheter-delivered to the site of an atherosclerotic lesion. The force generated by the expanding balloon expands the blocked lumen and compresses the blockage. Although balloon angioplasty provides increased blood flow in an obstructed lumen, the procedure often damages the surrounding arterial wall tissue. The biological response to this damage is a healing process, called restenosis, that often results in a renarrowing of the artery.

A preferred method for addressing restenosis is the localized delivery of biologically active solutes to the damaged tissue. This localized approach is attractive because doses that are higher than those achievable by systemic delivery are obtained. As a result, potential problems associated with biologically active solutes, such as toxicity, are minimized. Furthermore, biologically active solutes that are expensive or difficult to obtain, such as genetic modifiers, are used in an efficient manner. By way of the solute delivery system of the present invention, biologically active solutes are used as solutes in thermosensitive hydrogels to obtain such localized drug delivery.

The biologically active solutes used in the present invention include, for example, pharmaceutically active compounds, proteins, oligonucleotides, genes, DNA compacting agents, gene/vector systems, nucleic acids, and viral, liposomes and cationic polymers that are selected from a number of types depending on the desired application. For example, biologically active solutes include anti-thrombogenic agents such as heparin, heparin derivatives, urokinase, and PPack (dextrophenylalanine proline arginine chloromethylketone); anti-proliferative agents such as enoxaprin, angiopeptin, or monoclonal antibodies capable of blocking smooth muscle cell proliferation, hirudin, and acetylsalicylic acid; anti-inflammatory agents such as dexamethasone, prednisolone, corticosterone, budesonide, estrogen, sulfasalazine, and mesalamine; antineoplastic/antiproliferative/anti-miotic agents such as paclitaxel, 5-fluorouracil, cisplatin, vinblastine, vincristine, epothilones, endostatin, angiostatin and thymidine kinase inhibitors; anesthetic agents such as lidocaine, bupivacaine, and ropivacaine; anti-coagulants such as D-Phe-Pro-Arg chloromethyl keton, an RGD peptide-containing compound, heparin, antithrombin compounds, platelet receptor antagonists, anti-thrombin anticodies, anti-platelet receptor antibodies, aspirin, protaglandin inhibitors, platelet inhibitors and tick antiplatelet peptides; vascular cell growth promotors such as growth factor inhibitors, growth factor receptor antagonistss, transcriptional activators, and translational promoters; vascular cell growth inhibitors such as growth factor inhibitors, growth factor receptor antagonists, transcriptional repressors, translational repressors, antisense DNA, antisense RNA, replication inhibitors, inhibitory antibodies, antibodies directed against growth factors, bifunctional molecules consisting of a growth factor and a cytotoxin, bifunctional molecules consisting of an antibody and a cytotoxin; cholesterol-lowering agents; vasodilating agents; and agents which interfere with endogenous vascoactive mechanisms. These and other compounds are added to the gel using similar methods and routinely tested as set forth in the specification. Any modifications are routinely made by one skilled in the art.

Polynucleotide sequences useful in practice of the invention include DNA or RNA sequences having a therapeutic effect after being taken up by a cell. Examples of therapeutic polynucleotides include anti-sense DNA and RNA; DNA coding for an anti-sense RNA; or DNA coding for tRNA or rRNA to replace defective or deficient endogenous molecules. The polynucleotides of the invention can also code for therapeutic polypeptides. A polypeptide is understood to be any translation product of a polynucleotide regardless of size, and whether glycosylated or not. Therapeutic polypeptides include as a primary example, those polypeptides that can compensate for defective or deficient species in an animal, or those that act through toxic effects to limit or remove harmful cells from the body. In addition, the polypeptides or proteins that can be incorporated in the gels, or whose DNA can be incorporated, include without limitation, angiogenic factors including acidic and basic fibroblast growth factors, vascular endothelial growth factor, epidermal growth factor, transforming growth factor α and β, platelet-derived enotheial growth factor, platelet derived growth factor, tumor necrosis factor α, hepatocyte growth factor and insulin like growth factor; growth factors; cell cycle inhibitors including CD inhibitors; thymidine kinase ("TK") and other agents useful for interfering with cell proliferation, including agents for treating malignancies.

Figure 1B:
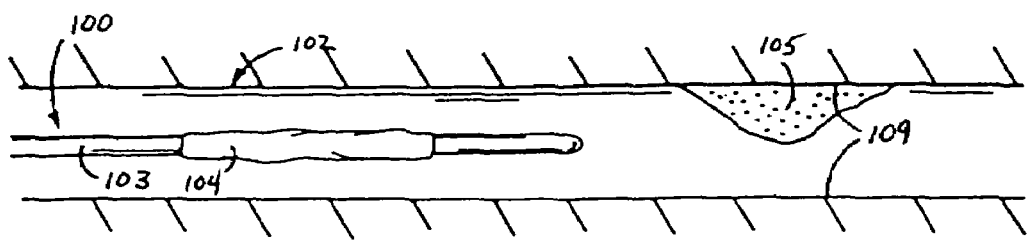
FIG. 1b shows the insertion of a solute-loaded hydrogel-coated balloon catheter into a body lumen, in accordance with an embodiment of the present invention.
Figure 1C:
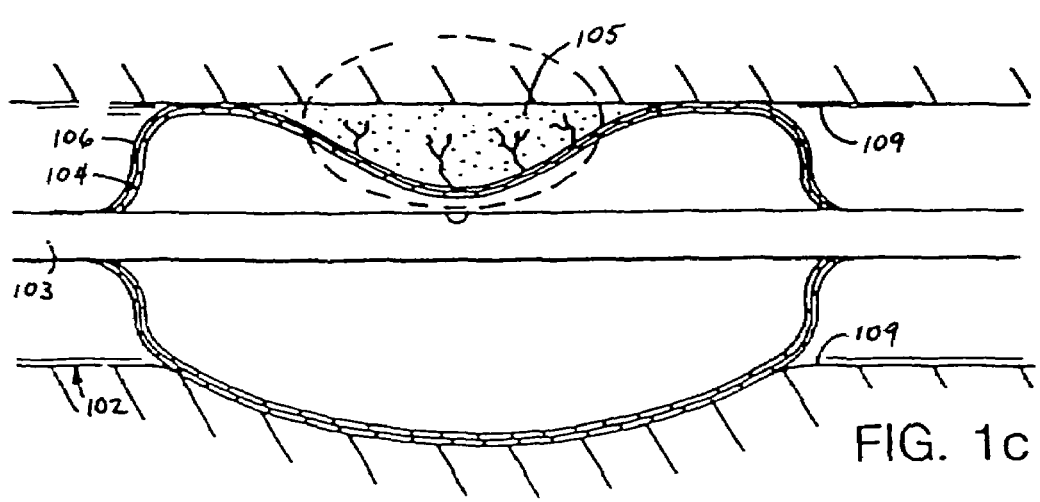
FIG. 1c shows the expansion of a solute-loaded hydrogel-coated balloon catheter at an occlusion site within a body lumen, in accordance with an embodiment of the present invention.

Referring now to FIGS. 1a-1c, an embodiment for the localized delivery of biologically active solute to a predetermined location within the body is described. The solute administration method shown in FIGS. 1a-1c illustrates the use of the present invention in conjunction with an angioplasty process. A catheter device 100 comprises a body 103 having a balloon 104 attached at its distal end. The balloon is formed of any suitable material such as vinyl polymers such as polyethylene; polyesters such as polyethylene terephthalate; polyamides such as nylon; polyolefins and copolymers thereof (e.g., Selar, Pebax, Surlyn, Hytrel, etc.). The balloon is optionally a perfusion balloon, which allows blood to perfuse the catheter to prevent ischemia during delivery. The balloon 104 on the body 103 includes a coating 106 of thermosensitive cellulose ether gel. As shown in FIG. 1a, a solution 108 comprising a biologically active solute is impregnated into the gel coating 106 with the balloon in its substantially deflated state prior to insertion into the patient. During the impregnation of the biologically active solute, the gel is held at a temperature lower than the gel transition temperature such that it is in an expanded state. Alternatively, the biologically active solute may be directly incorporated into the gel coating 106 using organic solvents or during synthesis of the gel.

After the biologically active solute is absorbed or incorporated into the gel, the device 100 is inserted into a body lumen 102 and positioned at a target location, such as an occlusion due to a deposition of plaque 105 on the lumen wall tissue 109. The device 100 is moved along the vessel to position the balloon 104 at the occlusion site, as shown in FIG. 1c. The lumen may be, for example, a narrow, tortuous opening through which the catheter is passed by torquing or other known techniques. As shown in FIG. 1c, the balloon 104 is inflated to provide close contact between the drug-impregnated gel coating 106 and the surrounding plaque and tissue.

Once positioned to the target location, the temperature of the gel coating 106 is increased above its transition temperature by any suitable technique such as, for example, exposure to a warm external fluid such as saline solution or by heating the saline internally with a thermal balloon, as is known in the art. Alternatively, in the case of short arterial delivery times, the gel transition temperature is below body temperature such that no external heating means is necessary. The increase in temperature above the transition temperature results in the deswelling of the gel coating 106, which in turn results in the accelerated release of the biologically active solute from the coating 106.

Figure 2A:
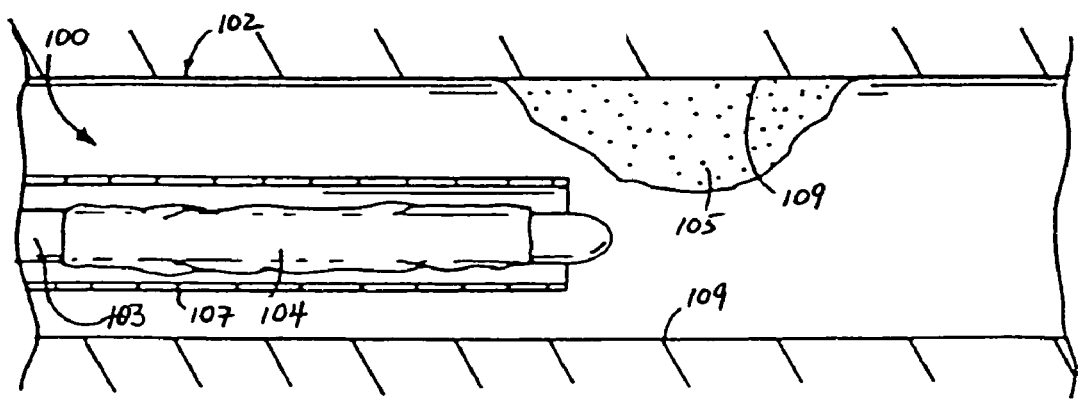
FIGS. 2a and 2b show a drug delivery balloon catheter embodiment of the present invention including a sheath for covering the catheter as it is being moved through a vessel toward an occlusion to be treated.
Figure 2B:
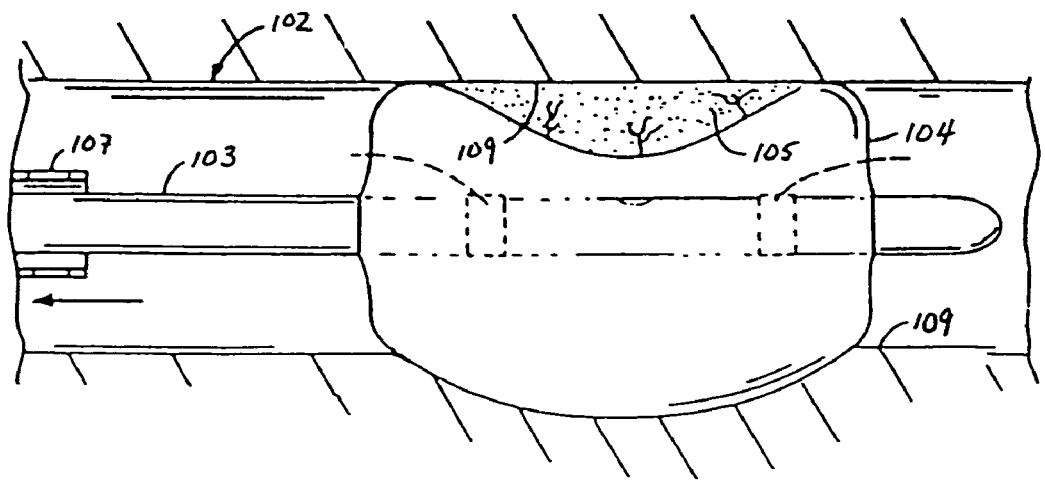

Referring to the embodiment of the invention illustrated in FIG. 2, the balloon portion 104 of catheter body 103 is optionally covered by a protective sheath 107 while the instrument 100 is inserted into a body lumen 102 and positioned at a target location. As the coated balloon 104 is positioned at occluded site 105, the protective sheath 107 is drawn back to expose the balloon 104. Alternatively, the sheath remains stationary while the catheter moves the coated balloon forward into the occluded region. The sheath 107 protects the coating and inhibits premature release of the biologically active solute. Such a sheath is particularly advantageous when the transition temperature of the gel coating 106 is less than body temperature, or when the biologically active solute (s) to be delivered is (are) highly toxic. In such cases, an advantage of a shrinking gel over a non-shrinking gel is the accelerated solute release rate, thus minimizing the required time for localized drug delivery.

Although FIGS. 1 and 2 illustrate the application of the present invention to an angioplasty process, the present invention is also used to administer biologically active solutes to target locations where there is no occlusive formation. Moreover, the present invention is not limited to use on balloon angioplasty devices, but is applicable to a variety of medical devices such as, for example, catheters, stents, blood filters, implants, artificial heart valves, oral dosage forms, suppositories and the like. Such medical devices may comprise metallic, polymer, or ceramic materials.

In one embodiment, the gel of the present invention is applied to a medical device that comprises a stent. As known in the art, stents are tubular support structures that are implanted inside tubular organs, blood vessels or other tubular body conduits. In the present invention, the stent is partially or completely coated with the solute-loaded hydrogel. The stent used with the present invention is of any suitable design, and is either self-expanding or balloon-expandable. The stent is made of any suitable metallic (e.g., stainless steel, nitinol, tantalum, etc.) or polymeric (e.g., polyethylene terephthalate, polyacetal, polylactic acid, polyethylene oxide—polybutylene terephthalate copolymer, etc.) material. The stent material, gel, and biologically active solute are selected to be compatible with each other. The gel is applied to the stent by any suitable method such as, for example, spraying the gel onto the stent or immersing the stent in the gel.

The present invention is further described with reference to the following non-limiting examples.

EXAMPLE 1

Release of Solute from Bonded PNIPA Gels

PNIPA gel was synthesized by the free radical solution copolymerization/crosslinking of PNIPA monomer. Approximately 9.6 g of NIPA monomer per 0.4 g of the crosslinker N,N'-methylenebisacrylamide was dissolved in 100 mL distilled water. Reagent grade ammonium persulfate ("APS") was used to initiate the reaction and reagent grade N,N,N',N'-tetramethylethylenediamine ("TEMED") was added as an accelerator. Freshly prepared initiator solutions were added to the solution to result in concentrations of 0.30 mg of APS per mL of monomer solution, and 0.15 mg of TEMED per mL of monomer solution. All solutions were degassed under 24 in Hg of vacuum for approximately 15 minutes.

The gels were synthesized in a glove box under a nitrogen atmosphere containing less than 2% oxygen. The initiators were added to the monomer solution and the solution was degassed under vacuum while stirring on a magnetic stirrer for 10-15 minutes.

Bonded gel membranes were made by casting gel solutions between glass plates separated by a high purity silicone rubber gasket. An impermeable plastic substrate (GELBOND® polyacrylamide support medium manufactured by FMC Bio-Products, Rockland Me.) having a thickness of approximately 0.2 mm was placed on one inside surface of the glass prior to gel casting. Gelation occurred within 1-2 hours, after which the molds were removed from the glove box and placed in a refrigerator at 32° C. for 24 hours to allow the reaction to approach completion. The resulting GELBOND® supported PNIPA membranes had thicknesses ranging from about 0.2 mm to 0.6 mm, when swollen in 25° C. water. After casting, the membrane samples were soaked in distilled water for approximately 72 hours to remove any unreacted compounds.

Three solutes were used to impregnate the PNIPA membrane samples: methyl orange dye (327 Da); 4,400 Da FITC-labeled dextrans ($M_w:M_n<1.5$); and 21,200 Da FITC-labeled dextrans ($M_w:M_n<1.25$). These solutes were selected, for example, because of their size, detectability by UV/VIS spectrophotometer, and ability to serve as models for therapeutic drugs.

The release behavior of solute from the GELBOND® supported PNIPA gel membranes was determined for each of the test solutes as a function of temperature, solute molecular weight, and gel swelling degree. Prior to solute loading, 2.54 cm×0.7 cm rectangular samples of gel coated GELBOND® film were prepared. The samples were placed in 3 mL of solution containing solute and HPLC grade water solution at 25° C. The solute concentration in the solution of methyl orange, 4,400 Da FITC-dextrans, and 21,200 Da FITC-dextrans was 1, 100, and 100 mg/mL, respectively.

Solute release tests were conducted using a modified HPLC system. Conventional HPLC systems typically consist of eluent reservoirs, a pump, an injector, a column, a detector, and an integrator. Eluent is pumped from the reservoirs through the pump, injector, column, detector and finally to waste in the order listed. A signal from the detector is collected by the integrator, as the eluent passes through the detector. In the modified system that was used to conduct the solute release tests, the injector and column of the typical HPLC system were replaced with a tubular sample chamber that was positioned between the eluent reservoirs and the pump, rather than between the pump and the detector. In addition, two eluent reservoirs that were heated to two different temperatures were used so that a step change in temperature could be initiated. The modified HPLC system consisted of two water baths, an HPLC switching valve, a custom tubular sample chamber, an HPLC pump, an UV-VIS detector, and a computer equipped with an integrator software package. Since the inner diameter of the tubular sample chamber was about 0.5 cm, the 0.9 cm×0.5 cm gel coated samples were mounted by sliding the sample into the center of the sample chamber. The sample chamber was then connected to the eluent reservoirs and pump with tygon and HPLC tubing. After a gel sample was mounted and the necessary connections were made, air was purged from the sample chamber and eluent line using standard HPLC priming techniques.

Once a sample was mounted and air was purged from the system, the solute release test was started by turning on the HPLC pump and activating the computer integration software. As the eluent passed from the detector, it was collected so that it could be used to determine the total amount of solute released from a sample during the course of an experiment. The total amount of solute that was released was calculated by multiplying the solute concentration in the collected eluent, determined using a UV-VIS spectrophotometer, by the total volume of eluent from the run. To determine total release from systems where release became too slow and thus was too dilute to be measured accurately, each gel sample was soaked in a 1.5 mL of HPLC-grade water after test completion to recover any solute retained by the gel. The total amount of solute in the HPLC-grade water was then determined by multiplying the solute concentration in the collected soaking solution, determined using a UV-Vis spectrophotometer, by the volume of soaking solution. This is added to the amount collected in the release test to yield the total release. The total release amount is also approximated by plotting the release as a function of temperature, and integrating the area under a release curve.

Solute release experiments were conducted under constant temperature and temperature step change conditions. Constant temperature experiments used eluent having temperatures of 24° C. and 34° C. (the transition temperature of PNIPA). Constant temperature experiments were performed by mounting a sample loaded with solute in the sample chamber and then allowing solute release by flowing solution past the gel at the desired test temperature causing drug release by simple diffusion. Step change experiments used eluent having an initial temperature of 24° C., which was increased to 34° C. or 41° C. after some amount of time into the test. In some tests, eluent temperature was decreased back to 24° C. after some time period at the increased temperature. This was done to determine if the release would resume to the rate at the time of the temperature increase.

Results from the PNIPA constant temperature tests conducted at 24° C. and 34° C. and the step change test conducted with a step in eluent temperature from 24° C. to 34° C. at t=0 showed that, for a given Q and solute size, the gel released between 94% and 98% of its solute load within the same time frame regardless of whether the test condition was 24° C., 34° C., or a step change in temperature from 24° C. to 34° C. Since the results of tests for all gel and solute combinations conducted at these temperatures exhibited similar solute release behaviors, the solute release characteristics of PNIPA appear to be independent of temperature from 24° C. to the gel's transition temperature of 34° C. This was expected because PNIPA gel's swelling degree changes modestly with temperature below its transition temperature. Thus, in this temperature regime, the gel does not release solute by shrinking significantly nor does it block release due to declining permeability.

Unlike lower test temperatures, test temperatures higher than 34° C. showed that PNIPA gels blocked solute release with varying degrees of effectiveness when the gels were contacted with an eluent having a temperature of 41° C. Up to 79% of the solute load was retained after about 25 minutes of isothermal exposure to eluent at 41° C. However, retention of the solute during step change experiments was slightly lower than during constant temperature experiments because a significant portion of solute load was released by diffusion prior to the increase in eluent temperature, which (release by diffusion) was thereafter inhibited.

Figure 3:
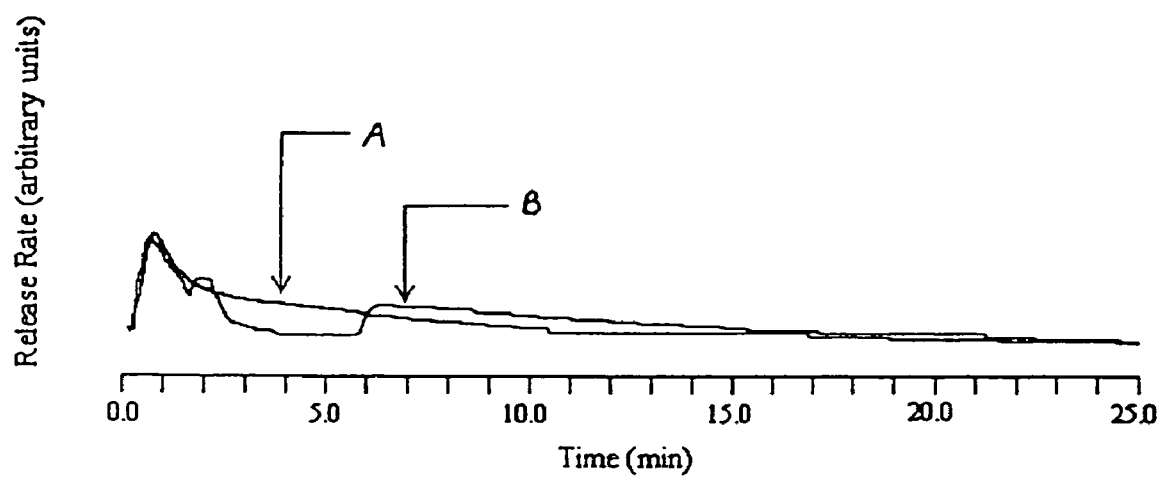
FIG. 3 shows the on/off solute release results of 4,400 Da FITC-dextran from PNIPA gel, in accordance with an embodiment of the present invention.
Figure 4A:
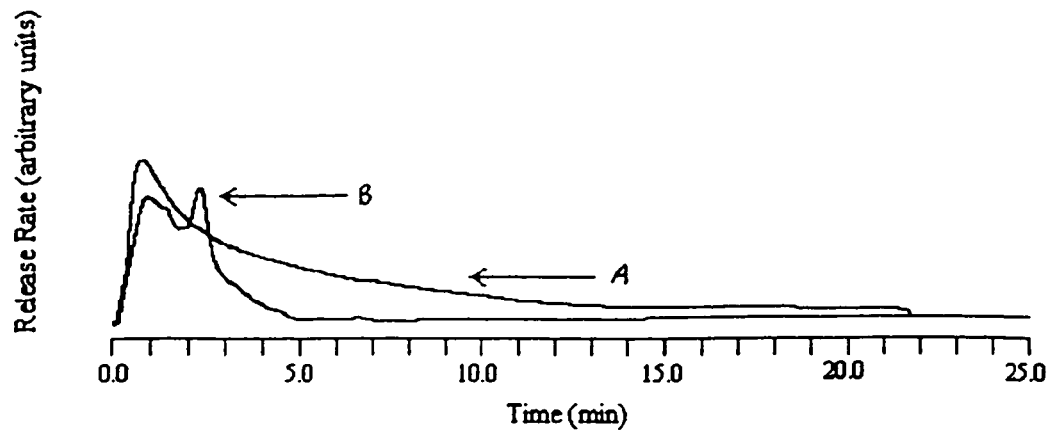
FIGS. 4a-4c show the release profile of solute having a molecular weight of 327 Da, 4,400 Da, and 21,200 Da from PNIPA gel having a Q of 18.
Figure 4B:
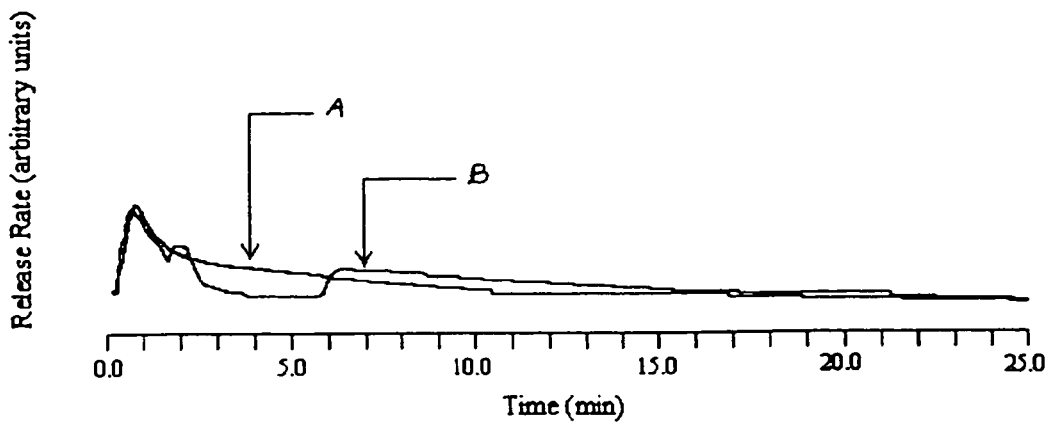
Figure 4C:
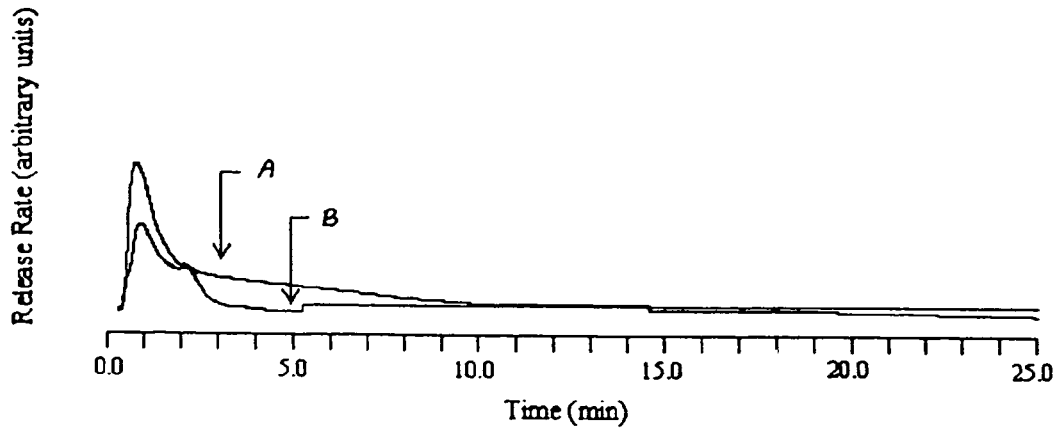
Figure 5A:
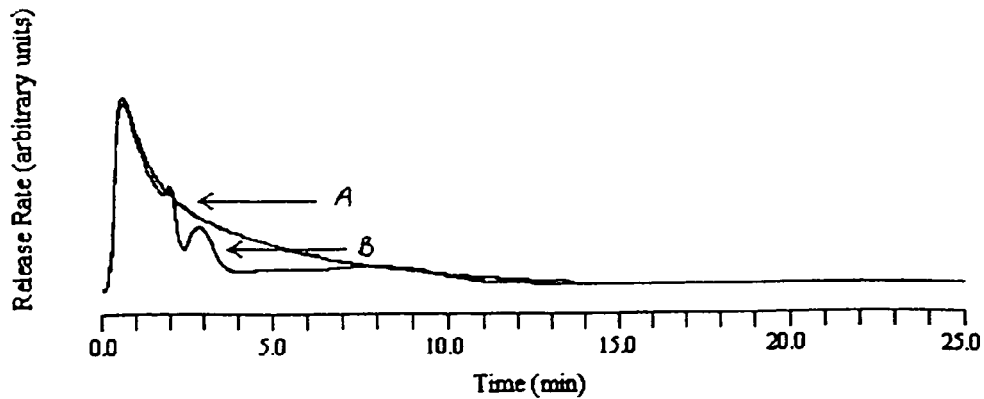
FIGS. 5a-5c show the release profile for solutes having molecular weights of 327 Da, 4,400 Da, and 21,200 Da, respectively, from PNIPA gel having a Q of 38.
Figure 5B:
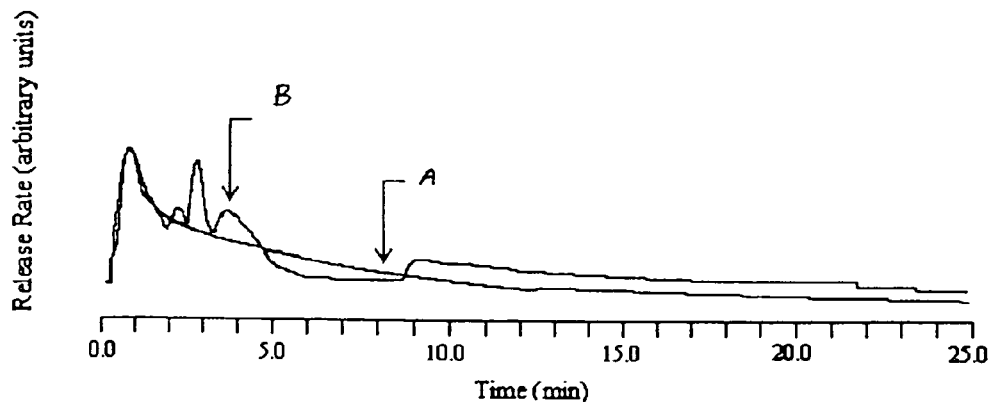
Figure 5C:
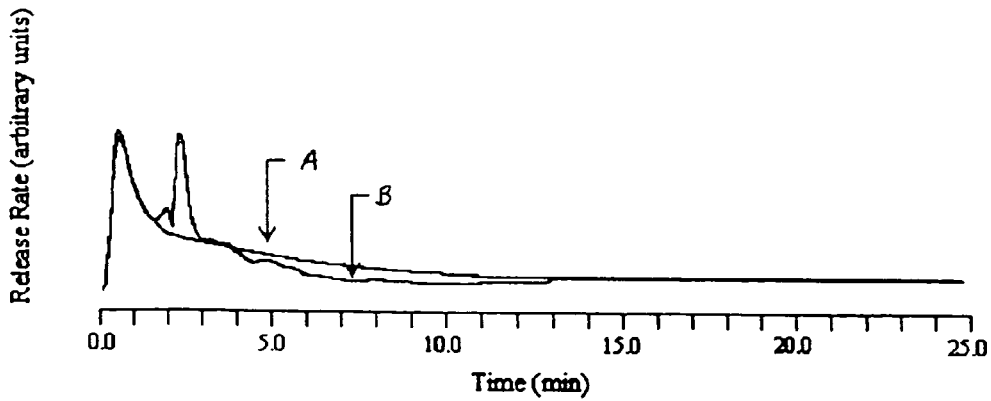

As an example, FIG. 3 shows the results of test a for 4,400 FITC-dextran released from a gel having a Q of 18 at a constant temperature of 24° C. and under 24-41-24° C. step change conditions. FIG. 3 illustrates PNIPA gel's ability to provide temperature control on/off solute release. In the figure, curve A represents the isothermal release profile at 24° C., and curve B represents a release profile for PNIPA gel having an initial temperature of 24° C. and being raised from 24° C. to 41° C. at two minutes and then lowered from 41° C. to 24° C. at six minutes. Whereas curve A illustrates that solute release declines continuously as expected for ordinary diffusional release under isothermal conditions where the temperature is less than the transition temperature of PNIPA, curve B illustrates that solute release substantially stops upon exceeding the transition temperature. Curve B further illustrates that after the solute release is stopped, it can be restarted by decreasing the temperature to below the transition temperature. This on/off solute release behavior is attributed to the finding that the permeability of solute in PNIPA is greatly decreased when it deswells (i.e., when increased to above its transition temperature), thus "trapping" the solute.

The results of the solute release tests can be seen by inspection of FIGS. 4a-4c and 5a-5c, which show the results of PNIPA solute release tests for Q=18 and Q=38, respectively (in all figures, curve A represents the release profile for isothermal conditions at 24° C., and curve B represents the release profile for temperature step conditions wherein the gel temperature was increased from 24° C. to 41° C. after two minutes into the test). FIGS. 4a and 5a, 4b and 5b, and 4c and 5c show the results of tests wherein the solute molecular weight was 327 Da, 4,400 Da and 21,200 Da, respectively.

The results indicate that both Q and solute size had an effect on solute release. For example, a PNIPA gel having a Q of 18 released only 57% of its solute load of 4,400 FITC-dextran after about 25 minutes when exposed to isothermal eluent at 24° C. (i.e., no shrinking of the gel), whereas a gel having a Q of 38 released a total of 94% of its solute load under the same release conditions. Upon heating to above its transition temperature, PNIPA of both Q values effectively blocked solute release until the gel was cooled again to below the transition temperature. The amount of solute released from PNIPA can thus be reduced by shortening the time prior to causing the temperature trigger.

The size of the solute material also had an effect on release behavior. The transient irregularities in release of solute (resulting from heating above the transition temperature of PNIPA (34° C.) and thus causing deswelling) were less pronounced with an increase in solute molecular weight for PNIPA having a Q of 18, whereas such solute release increased with an increase in solute molecular weight for PNIPA having a Q of 38. Hence, an increase in gel swelling renders the gel somewhat less effective in blocking solute release when the gel is heated above its transition temperature. In general, however, all PNIPA gels substantially blocked solute release when heated above the PNIPA transition temperature of 34° C. Finally, the percentage of solute that is retained by PNIPA gel, regardless of Q, increased with increasing solute molecular weight.

As mentioned, all PNIPA gels substantially blocked solute release when heated above the PNIPA transition temperature of 34° C. As can be seen in FIGS. 4a-4c and 5a-5c, however, an increase of temperature to above the PNIPA transition temperature often resulted in a transient pulse, or a series of pulses, of solute release before the solute release is blocked. Such pulses were of limited duration, however, such that the gels having a temperature triggered release typically released less solute than those held at an isothermal temperature below the transition temperature. The released of solute in the triggered release tests was caused by the efflux of solution carrying solute due to initial shrinking before permeability dropped sufficiently to inhibit release. A summary of percent of loaded solute that was released from PNIPA gel, as a function of Q, solute molecular weight, and release temperature, is provided in Table I. The data in this table illustrates that, for constant Q and solute molecular weight conditions, substantially less solute was released in the temperature triggered release tests than in the isothermal tests, even though the triggered release was often accompanied by a short-term convective release pulse or series of pulses. Thus it is clearly demonstrated that increasing temperature inhibits release in PNIPA. This is consistent with theory and experimental precedent in the literature for shrinking gels.

TABLE I

Summary of percent of loaded solute that was released from PNIPA gel, as a function of Q, solute molecular weight, and release temperature.

| Q | Solute MW (Da) | Temp (° C.) | % Solute Released after about 25 minutes |
|---|---|---|---|
| 18 | 327 | 24 | 94 |
| " | " | 24-41 | 45 |
| 38 | " | 24 | 97 |
| " | " | 24-41 | 79 |
| 18 | 4,400 | 24 | 57 |
| " | " | 24-41 | 70 |
| 38 | " | 24 | 94 |
| " | " | 24-41 | 91 |
| 18 | 21,200 | 24 | 74 |
| " | " | 24-41 | 39 |
| 38 | " | 24 | 85 |
| " | " | 24-41 | 58 |

EXAMPLE 2

Release of Solute from Bonded HPC Gels

HPC gel was synthesized by chemically crosslinking hydroxypropyl cellulose. Specifically, about 1 gram of HPC polymer (Sigma Chemical Co., 100,000 Da) was dispersed in about 10 mL of aqueous sodium hydroxide solution (pH 12) while stirring the solution until all polymer was thoroughly wetted. The solution was covered with PARAFILM® and 24 hours was allowed for complete polymer hydration. Divinylsulfone ("DVS") was added by micropipette and the solution stirred with a spatula. After mixing in the DVS, the solution was transferred to polypropylene centrifuge tubes and centrifuged at about 11,800×g for 1 hour to remove any air bubbles entrapped in the solution. The solutions were removed from the centrifuge tubes about 24 hours after the addition of divinylsulfone and placed in distilled water acidified by addition of hydrochloric acid to neutralize excess sodium hydroxide. The water was changed at 24 hour intervals for four to five days until the solution pH was constant to leach any unreacted reagents remaining in the gel. Details on a procedure for the formation of HPC gel is described in D. C. Harsh and S. H. Gehrke, "Controlling the Swelling Characteristics of Temperature-Sensitive Cellulose Ether Hydrogels," 17 *Journal of Controlled Release* 175-86 (1991), which is incorporated herein by reference.

Bonded gel membranes were made by casting gel solutions between glass plates separated by a high purity silicone rubber gasket. An impermeable plastic substrate (GELBOND® agarose support medium manufactured by FMC BioProducts, Rockland Me.) having a thickness of approximately 0.1 mm was placed on one inside surface of the glass prior to gel casting. The resulting substrate supported PNIPA membranes had thicknesses ranging from 0.1 mm to 0.6 mm, when swollen in 25° C. water.

The membrane samples were soaked in distilled water for approximately 72 hours to remove any unreacted compounds. The samples were thereafter soaked in a pH=2 solution of distilled water and HCl for about 24 hours to neutralize any excess NaOH. The samples were then soaked in distilled water for about 48 hours to remove any unreacted compounds.

Four solutes were used to impregnate the HPC membrane samples: methyl orange dye; 4,400 Da FITC-labeled dextrans ($M_w$:$M_n$<1.5); 21,200 Da FITC-labeled dextrans ($M_w$:$M_n$<1.25); and 50,700 Da FITC-labeled dextrans ($M_w$:$M_n$<1.25). These solutes were selected, for example, because of their size, detectability by UV-VIS spectrophotometer, ability to serve as models for biologically active solutes.

Solute release tests were conducted in the same manner as for PNIPA gels, as described in Example 1. The solute release experiments were designed to model the actual conditions of catheter use, which entail therapeutic solute loading at room temperature (25° C.), insertion of the catheter into the patient at 37° C., and temperature induced enhanced solute release when the catheter is placed at a target location in the body. While the experimental design was generally successful in modeling the actual use of catheter, heat lost to the experimental apparatus tubing reduced the 37° C. test temperature to 33° C. Because the transition temperature of HPC is fairly sharp (in this case, 43° C.), the reduction of test temperature from 37° C. to 33° C. had little impact on the test results.

Solute release experiments were conducted under four constant temperature conditions and three step change conditions. Constant temperature experiments used eluent having temperatures of 33° C., 41° C., 48° C., or 55° C. Thus, test temperatures below and above the transition temperature of HPC (43° C.) were used.

Constant temperature experiments were performed by mounting a sample, loaded with solute at 24° C., in the sample chamber and then triggering solute release by flowing solution past the gel at the desired test temperature. Step change experiments used eluent having an initial temperature of 33° C., increasing to 41° C., 48° C., or 55° C. at one or three minutes into a test.

The solute release experiments demonstrated that HPC gel, in contrast to PNIPA, did not block solute release when the gel was heated above its transition temperature. Instead, HPC gel exhibited sustained convective solute release upon reaching the transition temperature of HPC (43° C.), followed by continuing release at an accelerated rate until near-depletion of solute from the gel. The triggered solute release mechanism for HPC is thus different than for PNIPA, which is characterized by the substantial blocking of solute release after reaching its transition temperature. The convective solute release from HPC was observed for solutes ranging in molecular weight from 327 Da to 50,700 Da, with the effect dramatically increasing with solute size.

Figure 6:
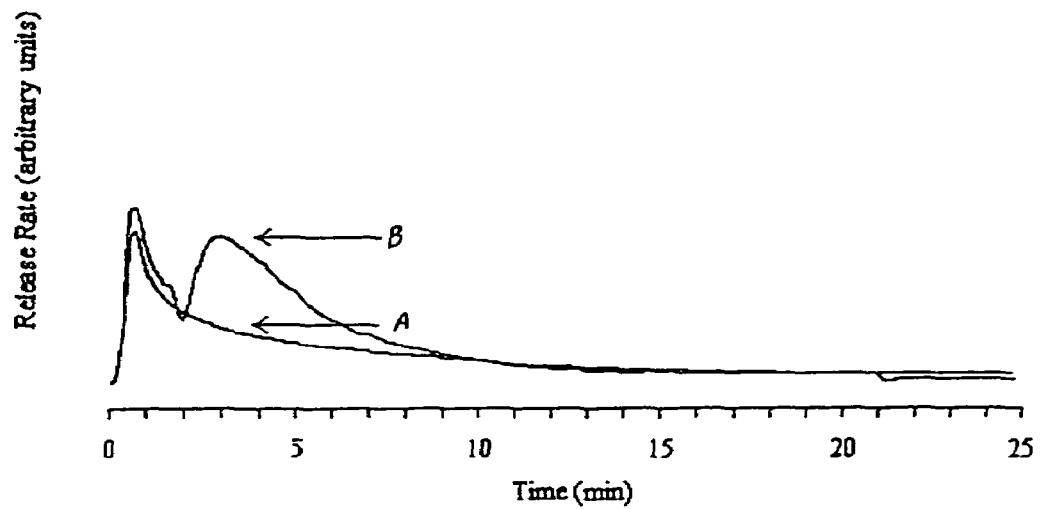
FIG. 6 shows the temperature triggered release of 4,400 Da FITC-dextran from HPC gel having a Q of 47, in accordance with an embodiment of the present invention.
Figure 7:
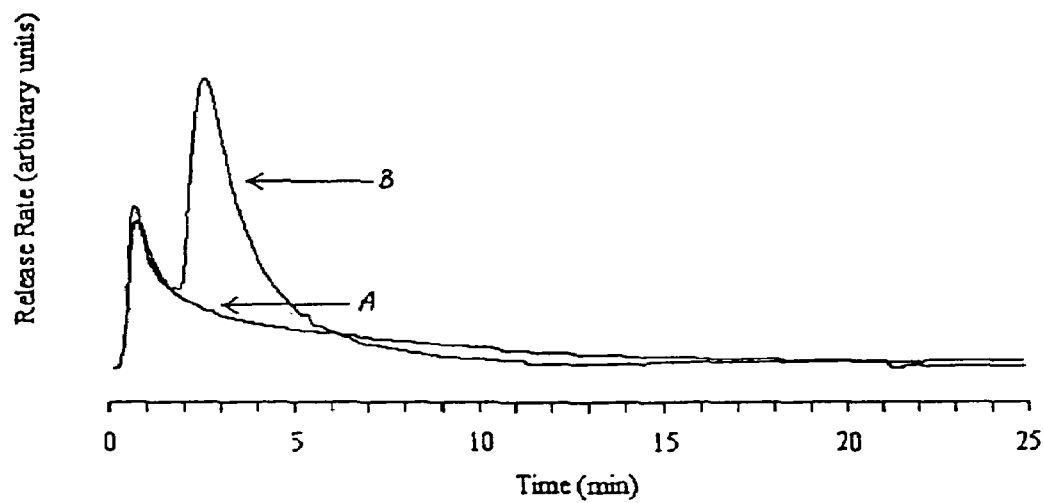
FIG. 7 shows the temperature triggered release of 4,400 Da FITC-dextran from HPC gel having a Q of 47, in accordance with another embodiment of the present invention.
Figure 8A:
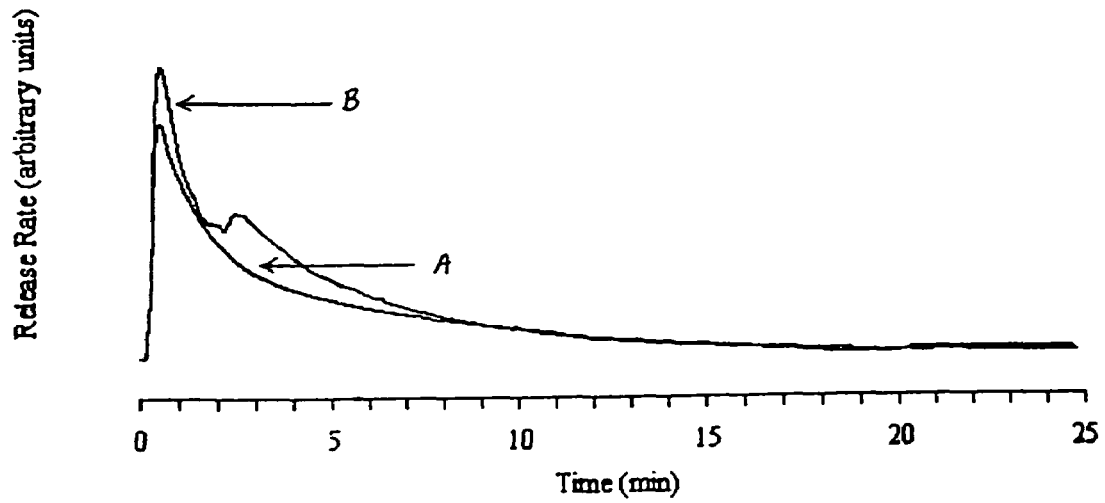
FIGS. 8a-8d show the release profiles for solutes having molecular weights of 327 Da, 4,400 Da, 21,200 Da, and 50,700 Da, respectively, from HPC gel having a Q of 47.
Figure 8B:
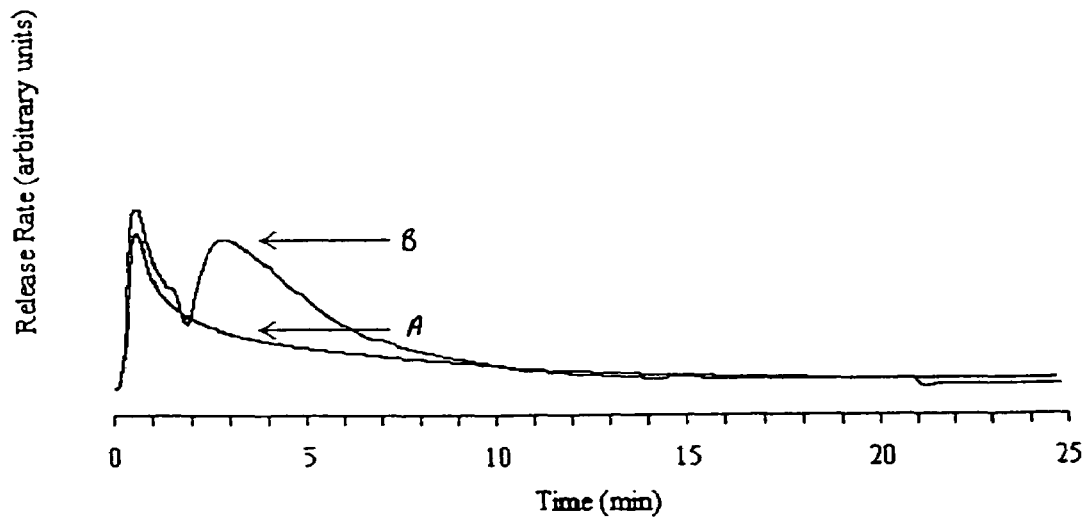
Figure 8C:
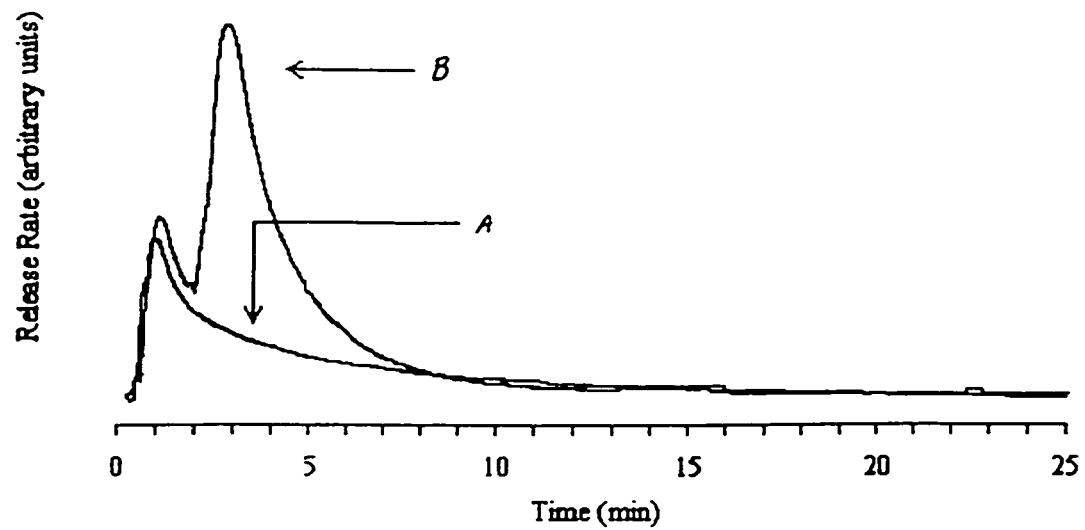
Figure 8D:
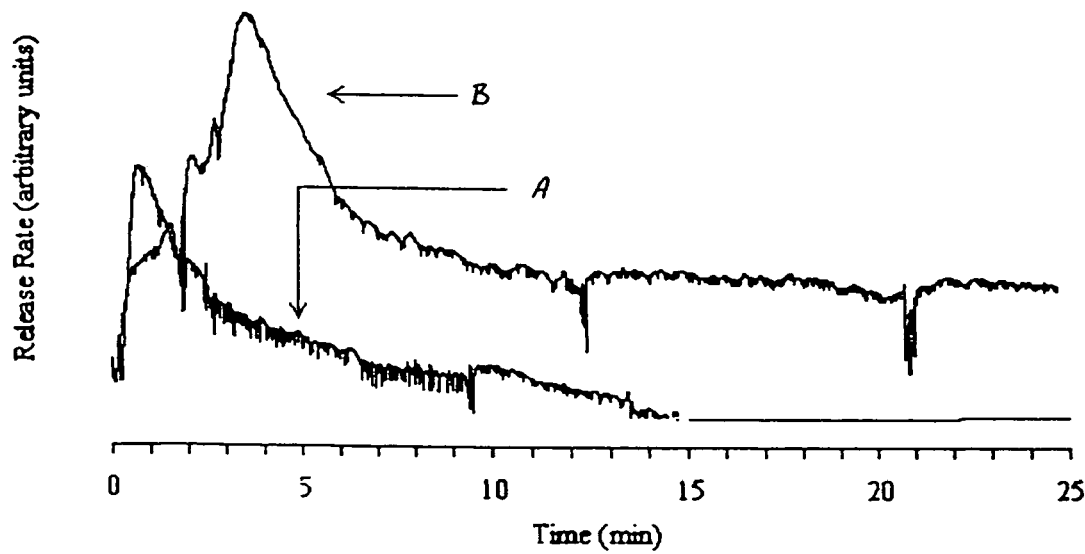

FIGS. 6 and 7 illustrate the ability of HPC gel to provide enhanced solute release when the gel is heated above its transition temperature and the effect of increasing trigger temperature on solute release rate. The solute used to produce the results plotted in FIGS. 6 and 7 was 4,440 Da FITC-dextran from a 500 micron thick HPC gel coated plastic substrate. In FIG. 6, curve A represents the release rate profile when the gel temperature is raised from 25° C. to 33° C. at t=0; and curve B represents the release rate profile when the gel temperature is raised from 25° C. to 33° C. at t=0 and from 33° C. to 48° C. at t=2 minutes. In FIG. 7, curve A represents the release rate profile when the temperature is raised from 25° C. to 33° C. at t=0; and curve B represents the release rate profile when the gel temperature is raised from 25° C. to 33° C. at t=0 and from 33° C. to 55° C. at t=2 minutes. In FIG. 6, the gel released 27% of its solute load before the step change in temperature from 33° C. to 48° C. was initiated. When the step change was initiated, the release rate of solute increased substantially. The increase in release temperature from 48° C. to 55° C. resulted in FIG. 7, which shows that the solute release rate increased even more dramatically. The increased release rate is believed to be due to the faster heat transfer and somewhat greater deswelling at the higher temperature. It should be noted, however, that the total amount of solute released after about 25 minutes increased only modestly because more than 98% of the solute load was released at 48° C.

The effect of solute size on release behavior can be seen by inspection of FIGS. 8a-8d, which show the release profiles for solutes having molecular weights of 327 Da; 4,400 Da; 21,200 Da; and 50,700 Da, respectively (in all figures, curve A represents the release profile for isothermal conditions at 33° C., and curve B represents the release profile for temperature step conditions wherein the gel temperature was increased from 33° C. to 55° C. after two minutes into the test). These figures illustrate that the convective solute release triggered by an increase in temperature above the gel transition temperature increases dramatically with an increase in solute molecular weight. While not wishing to be bound by theory, it is believed that this effect is due to a lower diffusivity of large solutes in the gel, and thus the convective component of release is larger relative to the diffusive component for large solutes. The noise visible in FIG. 8d was due to the limited amount of 50,700 Da FITC-dextran that partitioned into the gel and the slower diffusion rate leading to lower absolute rates.

In summary, all HPC gel and solute combinations exhibited sustained convective solute release, the rate of which increased with eluent temperature if the eluent temperature exceeded the transition temperature of HPC (43° C.). Because over 90° of solute load is released when the temperature exceeded 43° C., however, further increases in temperature only resulted in a modest increase in the total amount of solute released during the test. It was also noted that temperature triggered solute release from HPC gels generally resulted in an increase in the percent of total solute released when compared with isothermal tests. A summary of the percent of loaded solute that was released from HPC gel, as a function of Q, solute molecular weight, and release temperature, is presented in Table II. The data in this table illustrates that, for constant Q and solute molecular weight considerations, more solute was released in the temperature triggered release tests than the isothermal tests. The enhanced release of solute in the temperature triggered release tests is attributed to the broad, sustained convective release pulses associated with these tests. Moreover, as can be seen by the area under the release profile curves in FIGS. 6, 7 and 8a-8d, the temperature triggered release of solute from HPC resulted in accelerated release for about 3-5 minutes after exceeding the transition temperature of HPC, when compared with the isothermal tests in which the temperature was kept below the transition temperature of HPC (i.e., the HPC did not deswell).

TABLE II

Summary of percent of loaded solute that was released from HPC gel, as a function of Q, solute molecular weight, and release temperature.

| Q | Solute MW (Da) | Temp (° C.) | % Solute Released after about 25 min |
|---|---|---|---|
| 15 | 327 | 33 | 76 |
| " | " | 33-41 | 85 |
| 47 | " | 33 | 93 |
| " | " | 33-41 | 95 |
| 47 | 4,400 | 33 | 85 |
| " | " | 33-41 | 92 |

EXAMPLE 3

Release of Water-soluble Estradiol Complex

Figure 9:
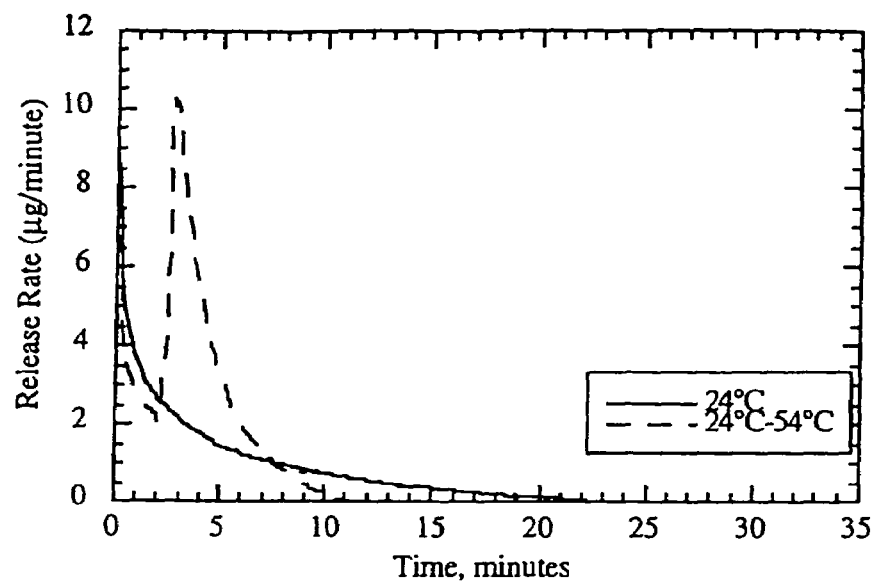
FIG. 9 shows a comparison of release rate curves for isothermal and temperature triggered release of estradiol complex from HPC gel, in accordance with an embodiment of the present invention.

HPC gel membrane samples having a thickness of approximately 0.66 mm were made as described in Example 2. These samples were impregnated with water-soluble estradiol complex (M.W. 980 Da) as solute. FIG. 9 shows a comparison of isothermal and temperature step change releases. In the figure, curve A represents the release profile for isothermal test conditions at 24° C., and curve B represents the release profile for temperature step change conditions where the temperature was increased from 24° C. to 54° C. after two minutes into the test. Curve B illustrates a large solute release convective pulse upon the temperature trigger at two minutes, thus resulting in a large amount of estradiol being released in a relatively short period of time. For the sample that underwent the temperature step change, about 77% of the estradiol was released within the first 7 minutes of the test: 18% before the temperature change and 59% in the five minutes immediately thereafter. In comparison, only about 40% of the estradiol was released in the isothermal test within the first 7 minutes of the test.

EXAMPLE 4

Release of Ovalbumin

Figure 10:
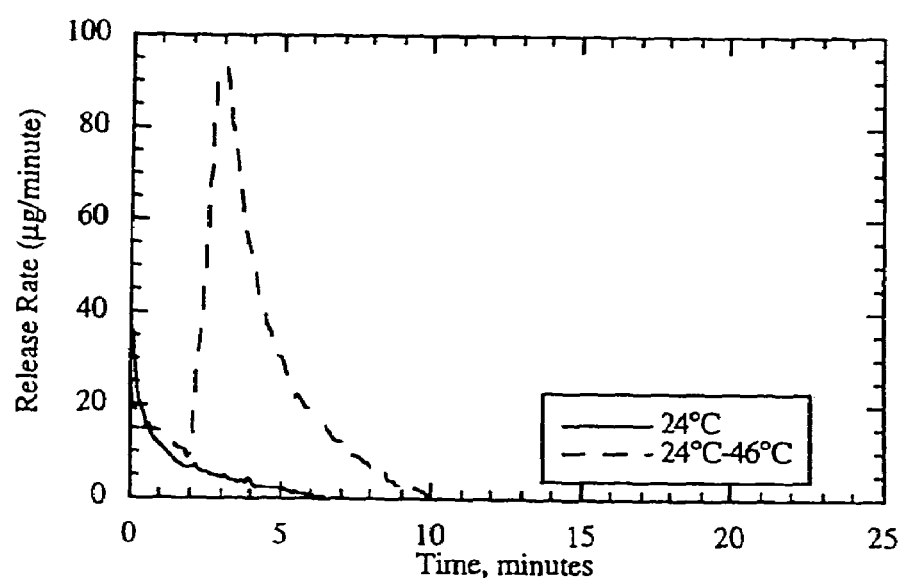
FIG. 10 shows a comparison of release rate curves for isothermal and temperature triggered release of ovalbumin from HPC gel, in accordance with an embodiment of the present invention.

HPC gel membrane samples having a thickness of approximately 0.66 mm were made as described in Example 2. These samples were impregnated with ovalbumin (M.w. 45,000 Da), which has been used as a model protein for bioactive proteins such as urokinase, as solute. Triggered release of ovalbumin was performed with a step change of 24° C. to 46° C. because ovalbumin has a denaturation temperature of about 56° C. As a result of the low triggering temperature used, the HPC gel did not fully deswell, thus reducing the amount of convective release. FIG. 10 shows a comparison of isothermal and temperature step change releases. In the figure, curve A represents the release profile for isothermal test conditions at 24° C., and curve B represents the release profile for temperature step change conditions where the temperature was increased from 24° C. to 46° C. after about two minutes into the test. Curve B illustrates a large solute release convective pulse upon the temperature trigger at two minutes, thus resulting in a large amount of ovalbumin being released in a relatively short period of time. For the sample that underwent the temperature step change, about 65% of the ovalbumin was released within the first 7 minutes of the test: 11% before the temperature change and 54% in the five minutes immediately thereafter. In comparison, only about 30% of the ovalbumin was released in the isothermal test within the first 7 minutes of the test.

Additionally, this example also proves that a useful effect is achieved for a gel that modestly deswells because the transition temperature of the gel is not reached. This is a useful finding because it suggests that biologically active solutes can be delivered even if the transition temperature of the gel is higher than is physiologically reasonable for use or above the denaturation temperature of the solute to be delivered.

EXAMPLE 5

Effect of Solute Molecular Weight on Triggered Release

On comparing triggered release behavior of solutes such as methyl orange (M.W. 327 Da), estradiol (M.W. 980 Da) and ovalbumin (M.W. 45,000 Da), it is observed that the ratio of the area of the convective pulse to the area of the isothermal release curve is much greater for ovalbumin than for methyl orange or estradiol. This suggests that the temperature trigger enhances the release of high molecular weight solutes to a greater extent than low molecular weight solute (see also FIGS. 8a-8d). While not wishing to be bound by theory, it is believed that the effect of solute molecular weight on release is due to the fact that larger solutes diffuse more slowly out of the gel than smaller solutes, and thus, the larger solutes are more influenced by gel deswelling.

EXAMPLE 6

Effect of Temperature on Triggered Release

Temperature triggered release experiments were performed using FITC-dextran as solute in HPC gel membranes. The temperature change was either 24° C. to 46° C. or 24° C. to 53° C. While 37% of the solute was released in the five minutes following the application of the 24° C. to 46° C. trigger, 65% of the solute was released in the same time period following the application of the 24° C. to 53° C. trigger. This difference in release characteristics may be explained by the difference in the volume change of the HPC gel (which is greater for the larger temperature step change), or because the gel shrinks faster with larger temperature step changes.

EXAMPLE 7

Triggered Release of Plasmid

Figure 11:
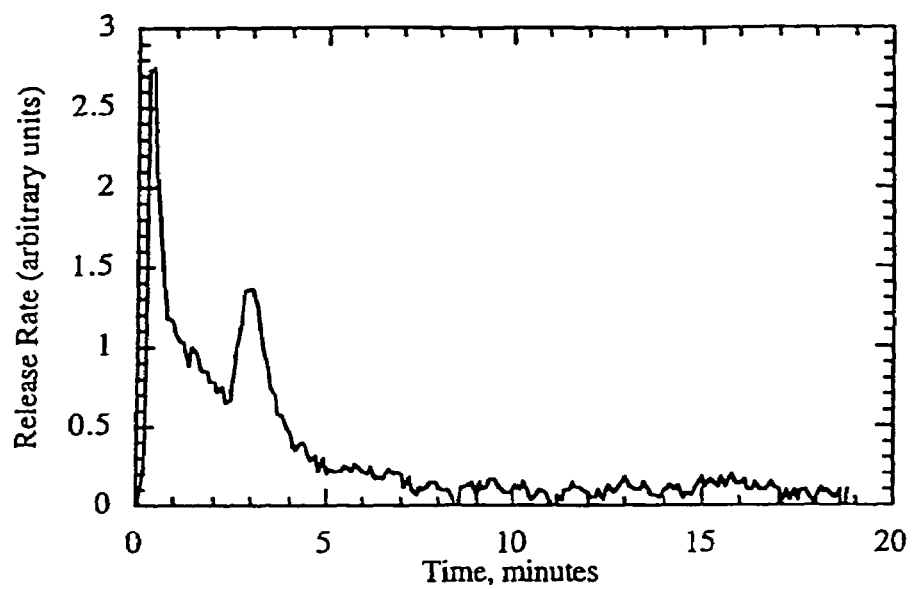
FIG. 11 shows the temperature triggered release of plasmid from HPC, in accordance with an embodiment of the present invention.

HPC gel membrane samples having a thickness of approximately 0.38 mm were made as described in Example 2. These samples were impregnated with pAdBM5 plasmid (approximately 9,000 base pairs) having an ApoE cDNA inserted at the BamHI site. Plasmid was used as solute to determine the effectiveness of delivering DNA via hydrogel delivery because gene therapy shows promise as a way to combat restenosis. FIG. 11 shows the temperature triggered release of the plasmid, where the temperature step change was 24° C. to 55° C. applied two minutes into the test. The size of the convective pulse was smaller than seen for other solutes, which is seemingly contrary to the release behavior of high molecular weight solutes such as ovalbumin. While not wishing to be bound by theory, one possible explanation for this discrepancy is that because plasmid has a very high molecular weight (about $6.6 \times 10^6$ Da), it is adsorbed onto the surface of the HPC gel rather than absorbed into it. The plasmid is thus rapidly released by diffusion since it is only adsorbed onto the surface. A small convective pulse is produced because some of the plasmid is eluted by the convective transport of water out of the gel when the gel deswells.

EXAMPLE 8

Coating Balloon Catheters with HPC Gel

A HPC gel was coated onto a polyethylene terephthalate ("PET") balloon catheter surface in a two step process.

In the first step, the balloon surface was derivatized with functional groups that could later be used to covalently bond with the HPC gel. To accomplish this objective, the balloon was first cleaned in acetone for about two hours and then rinsed with water. The balloon surface was then soaked for 24 hours in a 50% aqueous solution of ethylenediamine to create a primary amine as a functional group at the PET ester linkage. As is known in the art, functional groups such as amines or others are created on polymer surfaces by any other suitable technique, such as plasma treating. The balloon was then rinsed with water and allowed to dry in air.

In the second step, HPC was formed and bound to the substrate with a difunctional crosslinker to react with the amine groups on the balloon surface to thereby attach the HPC gel. To accomplish this objective, a 20% aqueous solution of HPC was prepared. To this solution, 5 N of NaOH was added at a ratio of about 40 µL/g of HPC. Divinylsulfone ("DVS"), a difunctional crosslinker, was then added at a ratio of about 40 µL/g of HPC. The vinyl groups of the DVS function to react with both the amine group on the surface of the balloon and the hydroxyl group of HPC. After mixing the solution, the balloon was immersed in the HPC solution for about 30 seconds, after which time it was removed and sealed with PARAFILM®. After about 24 hours, the balloon was placed in a 1 N HCl solution for about one hour to neutralize the residual base. The balloon was then placed in distilled water to leach any unreacted polymer and reagents.

Figure 12:
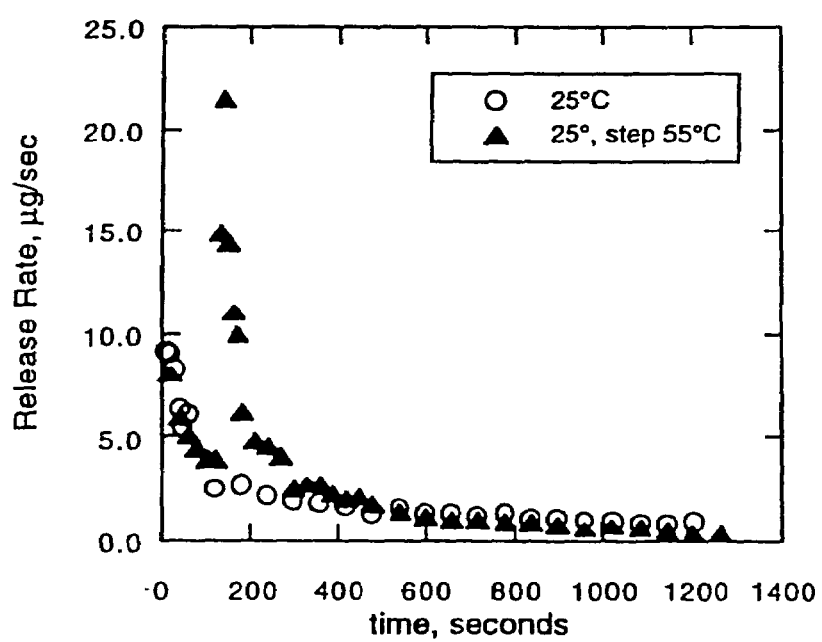
FIG. 12 shows a comparison of release rate curves for isothermal and temperature triggered release of methyl orange from an HPC gel-coated balloon catheter, in accordance with an embodiment of the present invention.

Release tests were conducted on the coated balloon using methyl orange dye as the solute. The HPC gel was loaded from a 2.5 mg/mL aqueous solution of methyl orange for about ten hours. Two release trials were performed using the same HPC gel coated catheter. The first trial was an isothermal test conducted at about 25° C. and the second trial involved a temperature step change from 25° C. to 55° C. after two minutes into the test. The results, as plotted in FIG. 12, demonstrate that the HPC coating is thermosensitive, as indicated by the increase in release rate after the temperature step change. These results are consistent with the observations for the model coatings as cited in other examples.

Comparison of PNIPA and HPC Release Characteristics

The inventors have shown that PNIPA gel exhibits on/off release characteristics for solutes ranging in molecular weight from 327 Da to 21,200 Da. When the temperature of PNIPA gel is increased above its transition temperature of 34° C., the gel releases only a slight amount of solute due to transitory convection and then blocks further solute release.

In contrast to PNIPA gel, HPC gel does not block solute release when exposed to temperatures higher than its transition temperature of 43° C. Instead, HPC gel exhibits substantial convective solute release for solutes ranging in molecular weight from 327 Da to 50,700 Da followed by diffusional solute release. The difference in release behavior of HPC and PNIPA gels is manifested, for example, in the percent of total solute that is released upon temperature triggered release. As shown in Table III, the triggered release of methyl orange dye, for example, resulted in significantly more solute released from HPC than from PNIPA, under similar test conditions. It is thus seen that the transitory convective pulses which often accompany the convective release (upon reaching the transition temperature) from PNIPA may not result in significant solute release due to the eventual blocking of solute release upon deswelling, whereas the convective release (upon reaching the transition temperature) from HPC-results in continued solute release of substantially all loaded solute.

TABLE III

Summary of percent of loaded solute that was released from PNIPA and HPC gels for the triggered release of methyl orange dye.

| Gel | Q | Solute MW (Da) | Temp (° C.) | % Solute Released after about 25 min |
|---|---|---|---|---|
| PNIPA | 18 | 327 | 24-41 | 45 |
| HPC | 15 | 327 | 33-41 | 85 |
| PNIPA | 47 | 327 | 24-41 | 15 |
| HPC | 38 | 327 | 33-41 | 95 |

Figure 13:
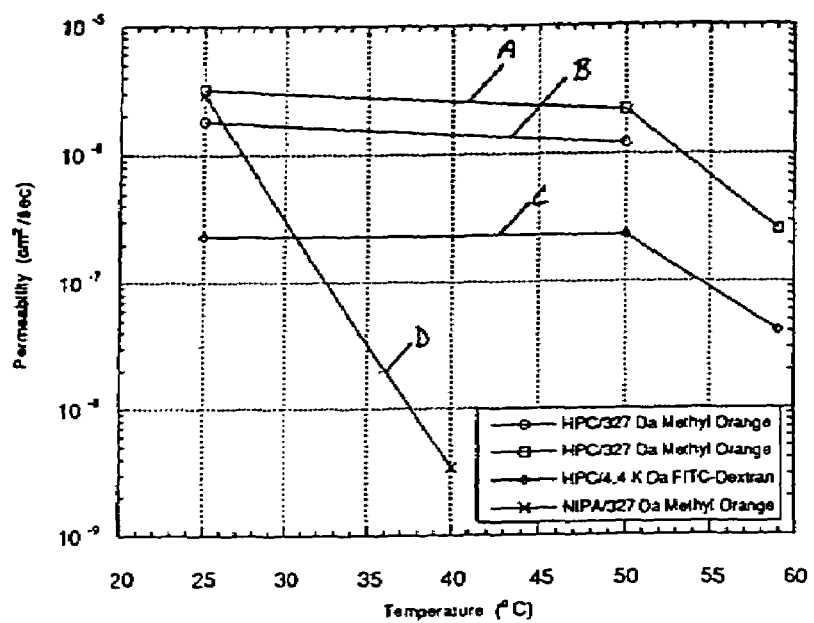
FIG. 13 shows permeability data for HPC and PNIPA gels as a function of temperature, in accordance with an embodiment of the present invention.

The differences in the release behaviors of HPC and PNIPA gels can be at least partially explained by the differences in the permeability of these gels to solute, as shown in FIG. 13. The inventors have found that the PNIPA gel decreases in permeability by as much as three orders of magnitude as the temperature is increased from below to above its transition temperature of 34° C. As a result, PNIPA "traps" solute when it deswells, as previously reported in the literature. In contrast, the permeability of HPC gels remains substantially constant (relative to the change in permeability of PNIPA) as the temperature is increased above its transition temperature of 43° C., despite significant deswelling comparable to that observed for PNIPA. In FIG. 13, curves A and B show the permeability of 327 Da methyl orange in HPC gel as a function of temperature, curve C shows the permeability of 4,400 Da FITC-dextran in HPC as a function of temperature, and curve D shows the permeability of 327 Da methyl orange in PNIPA as a function of temperature. The permeability was measured as described in the M.S. Thesis of James F. McBride, University of Cincinnati (Nov. 5, 1996), which is incorporated herein by reference. As can be seen by comparing curves A and D, the permeability of methyl orange in HPC decreased up to approximately one order of magnitude upon exceeding the transition temperature of HPC (43° C.), whereas the permeability of methyl orange in PNIPA decreased by three orders of magnitude upon exceeding the transition temperature of PNIPA (34° C.). In addition, a comparison of curves A and C proves that the result exists for solutes other than methyl orange.

Figure 14:
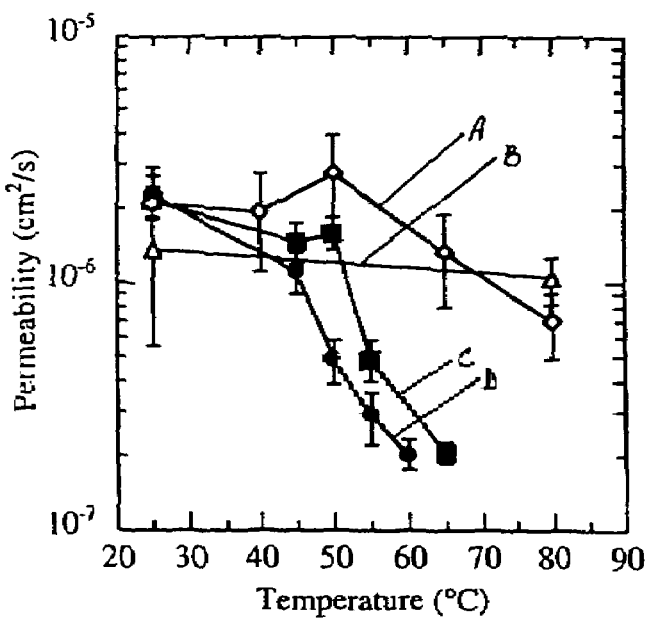
FIG. 14 shows permeability data for HPC and HPMC gels as a function of temperature, in accordance with an embodiment of the present invention.

FIG. 14 illustrates that the ability of cellulose gels to deswell while maintaining a substantially constant permeability is not limited to HPC. Specifically, HPMC gels were formed in the same manner as described in Example 2 for HPC, using an aqueous solution of HPMC polymer (Dow Chemical Co., Methocel E5, 70,000 Da). In FIG. 14, curves A and B show the permeability of 327 Da methyl orange in HPMC gel as a function of temperature, and curves C and D show the permeability of 327 Da methyl orange in HPC as a function of temperature. As can be seen by inspection of FIG. 14, the permeability of methyl orange in HPMC remained relatively constant over a broader range than for HPC—permeability decreased by about an order of magnitude in HPC gels when the temperature was increased from 25° C. to 65° C., while it decreased by less than half an order of magnitude in HPMC gels as temperature was increased from 25° C. to 80° C. despite significant deswelling comparable to HPC and PNIPA gels.

The ability of cellulose gels (e.g.; HPC gel) to expel large solutes by convection makes them desirable candidates for use with medical devices for the triggered delivery of biologically active solute. Moreover, the inventors have demonstrated that one of the advantages of coating a balloon catheter with cellulose gels lies in the ability of such gels to rapidly expel biologically active solutes when the gels are heated, particularly above their transition temperatures. The inventors have also shown that a temperature induced pulse of solute release is possible at almost any time after the solute has been absorbed into these gels. Furthermore, the size of a convective release pulse increases with an increase in temperature. In summary, the timing and magnitude of enhanced solute release from cellulose gels is controlled by, for example, controlling the temperature step change and the time at which it occurs.

The present invention provides a system and method for the delivery of solute to a target location using a thermosensitive cellulose gel structure. Although the present invention has been described with respect to several exemplary embodiments, there are many other variations of the above-described embodiments which will be apparent to those skilled in the art, even where elements have not explicitly been designated as exemplary. It is understood that these modifications are within the teaching of the present invention, which is to be limited only by the claims appended hereto.

What is claimed is:

1. A method of delivering solute to a target location, the method comprising the steps of:
    providing at least one cellulose;
    providing a substrate, wherein said substrate comprises a polymer material;
    providing functional groups on said polymer material;
    adding a crosslinking material to said cellulose, wherein said crosslinking material reacts with said cellulose and said functional groups and thereby forms a cellulose ether gel and attaches said cellulose ether gel to the substrate to form a cellulose ether gel structure;
    loading said cellulose gel structure with a solute;
    positioning said loaded gel structure to said target location; and
    increasing the temperature of said loaded gel structure from an initial temperature to a temperature at or above the transition temperature of said gel.

2. The method of claim 1, wherein:
    said polymer material is polyethylene terephthalate;
    said functional groups comprise amine groups; and
    said crosslinking material comprises divinylsulfone.

3. The method of claim 2, further comprising the step of exposing said polyethylene terephthalate to ethylenediamine to form said amine groups.

4. A method of delivering solute to a target location, the method comprising the steps of:
    providing a crosslinked thermosensitive cellulose ether gel structure, wherein said gel structure is loaded with a solute;
    coating said gel onto a substrate;
    positioning said loaded gel structure to said target location; and
    increasing the temperature of said loaded gel structure from an initial temperature to a temperature at or above the transition temperature of said gel,
    wherein:
    said target location is located within a mammalian body;
    said substrate is a medical device; and
    said solute is a biologically active solute.

5. The method of claim 4, wherein said step of increasing the temperature of said loaded gel structure is accomplished by exposing said loaded gel structure to an external liquid having a temperature greater than said initial temperature of said loaded gel structure.

6. The method of claim 4, wherein said step of increasing the temperature of said loaded gel structure is accomplished by exposing said loaded gel structure to body temperature.

7. A method of delivering solute to a target location, the method comprising the steps of:
    providing at least one cellulose;
    providing a substrate, wherein said substrate comprises a polymer material;
    providing functional groups on said polymer material;
    adding a crosslinking material to said cellulose, wherein said crosslinking material reacts with said cellulose and said functional groups and thereby forms a cellulose ether gel and attaches said cellulose ether gel to the substrate to form a cellulose ether gel structure;
    loading said cellulose ether gel structure with a solute;
    positioning said loaded gel structure to said target location; and
    increasing the temperature of said loaded gel structure from an initial temperature below the transition temperature of said gel to a temperature at or above the transition temperature of said gel, wherein said step of increasing the temperature of said loaded gel structure results in the deswelling of said gel and the release of said solute from said gel.

8. The method of claim 7, wherein:
    said polymer material is polyethylene terephthalate;
    said functional groups comprise amine groups; and
    said crosslinking material comprises divinylsulfone.

9. The method of claim 8, further comprising the step of exposing said polyethylene terephthalate to ethylenediamine to form said amine groups.

10. A method of delivering solute to a target location, the method comprising the steps of:
    providing a crosslinked thermosensitive cellulose ether gel structure, wherein said gel structure is loaded with a solute;
    coating said gel onto a substrate;
    positioning said loaded gel structure to said target location; and increasing the temperature of said loaded gel structure from an initial temperature below the transition temperature of said gel to a temperature at or above the transition temperature of said gel, wherein said step of increasing the temperature of said loaded gel structure results in the deswelling of said gel and the release of said solute from said gel, wherein:

said target location is located within a mammalian body;

said substrate is a medical device; and said solute is a biologically active solute.

11. The method of claim 10, wherein said step of increasing the temperature of said loaded gel structure is accomplished by exposing said loaded gel structure to an external liquid having a temperature greater than said initial temperature of said loaded gel structure.

12. The method of claim 10, wherein said step of increasing the temperature of said loaded gel structure is accomplished by exposing said loaded gel structure to body temperature.

* * * * *

UNITED STATES PATENT AND TRADEMARK OFFICE
CERTIFICATE OF CORRECTION

PATENT NO. : 7,407,671 B2
APPLICATION NO. : 10/787233
DATED : August 5, 2008
INVENTOR(S) : McBride et al.

It is certified that error appears in the above-identified patent and that said Letters Patent is hereby corrected as shown below:

Column 2, line 20, "Poly(N-isopropylacrtlamide-co-alkyl methacrylate)" should be changed to --Poly(N-isopropylacrylamide-co-alkyl methacrylate)--;
Column 4, line 20, "gels.," should be changed to --gels,--;
Column 4, lines 60-61, "viral, liposomes" should be changed to --viral liposomes--;
Column 5, line 9, "keton," should be changed to --ketone,--;
Column 5, line 11, "anticodies" should be changed to --antibodies--;
Column 5, line 14, "promotors" should be changed to --promoters--;
Column 5, line 15, "antagonistss" should be changed to ---antagonists--;
Column 5, line 24, "endogeneus vascoactive" should be changed to --endogenous vasoactive--; and
Column 5, line 47, "enotheial" should be changed to --endothelial--.

Signed and Sealed this

Eighth Day of September, 2009

David J. Kappos
*Director of the United States Patent and Trademark Office*